(12) United States Patent
Do et al.

(10) Patent No.: US 11,627,866 B2
(45) Date of Patent: Apr. 18, 2023

(54) METHOD FOR MANUFACTURING AN ENDOSCOPE INSERTION TUBE, AND ENDOSCOPE HAVING AN INSERTION TUBE

(71) Applicant: HOYA CORPORATION, Tokyo (JP)

(72) Inventors: Anh Minh Do, Friedberg (DE); Thomas Viebach, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 486 days.

(21) Appl. No.: 16/652,261

(22) PCT Filed: Oct. 15, 2018

(86) PCT No.: PCT/IB2018/001155
§ 371 (c)(1),
(2) Date: Mar. 30, 2020

(87) PCT Pub. No.: WO2019/077402
PCT Pub. Date: Apr. 25, 2019

(65) Prior Publication Data
US 2020/0237189 A1 Jul. 30, 2020

(30) Foreign Application Priority Data
Oct. 16, 2017 (DE) .......................... 102017123975.8

(51) Int. Cl.
*A61B 1/00* (2006.01)
*A61B 1/005* (2006.01)
(Continued)

(52) U.S. Cl.
CPC .......... *A61B 1/0011* (2013.01); *A61B 1/0055* (2013.01); *A61B 1/0057* (2013.01);
(Continued)

(58) Field of Classification Search
None
See application file for complete search history.

(56) References Cited

U.S. PATENT DOCUMENTS 5,438,975 A * 8/1995 Miyagi ............... A61B 1/0055
600/141
5,807,241 A * 9/1998 Heimberger ......... A61B 1/0055
600/142
(Continued)

FOREIGN PATENT DOCUMENTS

DE 10052679 A1 5/2001
EP 0764423 A1 3/1997
(Continued)

OTHER PUBLICATIONS

Office Action issued in Japanese Counterpart Patent Appl. No. 2020-518684, dated Jul. 5, 2022.
(Continued)

*Primary Examiner* — Timothy J Neal
(74) *Attorney, Agent, or Firm* — Greenblum & Bernstein, P.L.C.

(57) ABSTRACT

The invention relates to a method for manufacturing an endoscope insertion tube (2).The insertion tube (2) has a proximal passive flexible section (20) and a distal angled section (A). The entire insertion tube, including the passive flexible section (20) and the angled section (A), is formed from a single tube element. The invention further relates to an endoscope having such an insertion tube (2).

8 Claims, 12 Drawing Sheets

(51) Int. Cl.
  *B23K 26/08* (2014.01)
  *B23K 26/38* (2014.01)
(52) U.S. Cl.
  CPC .......... *A61B 1/00071* (2013.01); *B23K 26/08* (2013.01); *B23K 26/38* (2013.01)

(56) References Cited

U.S. PATENT DOCUMENTS

| | | | |
|---|---|---|---|
| 6,749,560 B1* | 6/2004 | Konstorum | A61B 1/00071 |
| | | | 604/525 |
| 2003/0009208 A1 | 1/2003 | Snyder et al. | |
| 2003/0199736 A1 | 10/2003 | Christopher | |
| 2009/0234191 A1 | 9/2009 | Kitagawa et al. | |
| 2009/0312603 A1 | 12/2009 | Lam et al. | |
| 2010/0287755 A1 | 11/2010 | Körner | |
| 2011/0112365 A1* | 5/2011 | Galperin | A61B 1/0055 |
| | | | 600/118 |
| 2011/0230718 A1 | 9/2011 | Akui | |
| 2013/0226151 A1 | 8/2013 | Suehara | |
| 2014/0053940 A1* | 2/2014 | Konstorum | A61M 25/0138 |
| | | | 138/118 |
| 2014/0163321 A1 | 6/2014 | Seto et al. | |
| 2014/0378767 A1* | 12/2014 | Lee | A61B 1/0011 |
| | | | 600/141 |
| 2017/0095138 A1 | 4/2017 | Nakade et al. | |
| 2019/0059700 A1* | 2/2019 | Matsuda | A61B 1/0057 |
| 2020/0237185 A1 | 7/2020 | Do et al. | |

FOREIGN PATENT DOCUMENTS

| | | |
|---|---|---|
| EP | 1401526 A2 | 3/2004 |
| EP | 2740400 A1 | 6/2014 |
| EP | 2777476 A1 | 9/2014 |
| JP | H06-084414 U | 12/1994 |
| JP | 2002-236260 A | 8/2002 |
| JP | 2009-240711 A | 10/2009 |
| TW | 201350075 A | 12/2013 |
| WO | 03/004086 A2 | 1/2003 |
| WO | WO2011/046002 A1 | 4/2011 |
| WO | 2013/190910 A1 | 12/2013 |
| WO | 2014/030437 A1 | 2/2014 |
| WO | WO2016/052145 A1 | 4/2016 |

OTHER PUBLICATIONS

International Search Report (ISR) dated May 29, 2019 filed in PCT/IB2018/001155.
German Office Action (DEOA) dated Oct. 2, 2018 for corresponding German (DE) Application No. 102017123975.8.
International Search Report dated May 28, 2019, issued in family member PCT/IB2018/001154.
Official Communication dated Jun. 9, 2022, issued in European family member 18796097.6.
Office Action issued in European Patent Office (EPO) Counterpart Patent Appl. No. 18797086.8, dated Jun. 14, 2022.
Third Office Action issued in related Chinese Patent Appl. No. 201880063676.1 dated Oct. 26, 2022, together with an English-language translation.
Second Office Action issued on related Japanese patent application No. JP2020-518811 dated Dec. 20, 2022, together with an English-language translation.
Office Action issued in United States Patent and Trademark Office U.S. Appl. No. 16/652,287, dated Sep. 21, 2022.

* cited by examiner

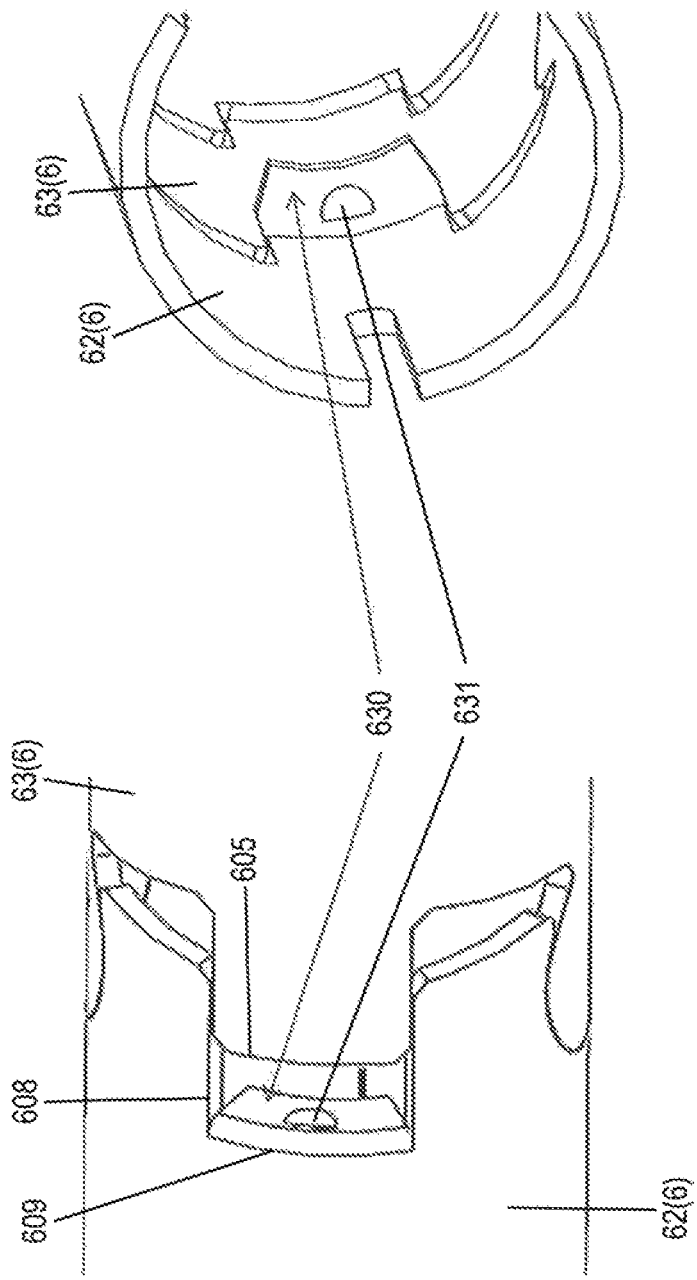

METHOD FOR MANUFACTURING AN ENDOSCOPE INSERTION TUBE, AND ENDOSCOPE HAVING AN INSERTION TUBE

The present invention relates to a method for manufacturing an endoscope insertion tube, and an endoscope having an insertion tube.

An endoscope is a device that may be used to examine the interior of living organisms, and also technical cavities. The flexible insertion tube is an important part of an endoscope. The demands on an insertion tube are considerable and numerous. On the one hand, it must be flexible to allow it to be introduced into the human body. On the other hand, the insertion tube must have a certain rigidity. During the examination, the medical practitioner must be able to push and turn the insertion tube by use of the control body. The insertion tube must be rigid enough that it does not become kinked or twisted. Therefore, conventional insertion tubes require a very complex construction and high manufacturing costs in order to meet the stated requirements.

To simplify the manufacture of a tube element for medical purposes and to lower the manufacturing costs, in the prior art the concept has arisen of manufacturing a tube element for medical purposes from a single hard tube. Various highly precise cuts are made on the hard tube with a laser cutting machine. Due to the cuts, a hard tube is flexible but can maintain rigidity. The flexibility and rigidity of the tube may be controlled via the shape, arrangement, and size of the cuts.

The object of the present invention is to provide a method for manufacturing an endoscope insertion tube and for providing an endoscope having an insertion tube, which are less complex and by means of which the costs may be even further reduced.

With regard to the method, the object is achieved by a method of the present disclosure. Advantageous refinements are described herein.

In the invention, in the method for manufacturing an endoscope insertion tube, the entire insertion tube, including the proximal passive flexible section and the distal angled section, is formed from a single tube element.

Thus, it is necessary to provide only one tube element. A joining operation between the proximal passive flexible section and the distal angled section is dispensed with. The production costs are lower than in previous methods for manufacturing an insertion tube.

In this method, the entire insertion tube, including the angled section, may be cut from a single tube element via laser. The machining by laser allows a very precise design of the overall insertion tube.

In this method, individual cuts may be made in the tube element, and the manufacture is simple and cost-effective.

In this method, the distal angled section has inwardly bent guide protrusions on which a traction cable is supported; the inwardly bent guide protrusions are cut from the circumferential wall of the distal angled section and then bent inwardly. In this way, guides for a traction cable are easily produced on the inner circumferential side of the angled section.

In this method, at the transition from the proximal passive flexible section and the distal angled section, the insertion tube has an inwardly bent bracket on which a guide spring is supported; the inwardly bent bracket is cut from the circumferential wall of the insertion tube and then bent inwardly. The number of inwardly bent brackets on which a guide spring is supported corresponds to the number of guide springs, and thus, to the number of traction cables. In this way, guides for guide springs are easily produced on the inner circumferential side of the insertion tube.

In this method, multiple articulated joints may be produced in the circumferential wall of the distal angled section by cutting. Individual articulated joints that form independent bodies and are joined together in a form-fit manner are easily and cost-effectively produced.

In this method, the particular articulated joint produced by cutting has a coupling section that is coupled to an adjacent articulated joint, produced by cutting, in such a way that an axial movement, but not a radial movement, of the articulated joints relative to one another is blocked, and a guide section that engages with an adjacent articulated joint, produced by cutting, in such a way that an axial movement of the articulated joints relative to one another is made possible. Adjacent articulated joints are coupled to one another via the coupling section, and adjacent articulated joints are axially movable relative to one another via the guide section.

In this method, the proximal passive flexible section is produced by respective lateral indentations that are provided perpendicular to the longitudinal extension of the tube element. The proximal passive flexible section may be quickly and easily manufactured in this way.

In this method, in the longitudinal extension of the tube element the proximal passive flexible section has at least two subsections which include the respective lateral indentations at different spacings from one another in the longitudinal extension of the tube element. Multiple separate subsections having different degrees of flexibility and bendability with respect to one another may thus be formed in the proximal passive flexible section.

In this method, the tube element may be made of stainless steel. The cuts may be easily made, and the material costs are low.

In this method, the tube element may be made of plastic. Any suitable plastic having sufficient strength may be used. The plastic only needs to be able to provide the bendability of the finished insertion tube.

In this method, from a control body situated proximally from the proximal passive flexible section, a traction cable may be situated on the inner circumferential side of the tube element, wherein at an articulated joint of the distal angled section situated farthest distally, the traction cable is led through a first slot in a wall of the tube element to the outer circumference of the tube element, around the outer circumference of the tube element, to a second slot in the wall of the tube element to the inner circumference of the tube element, wherein the second slot is opposite the first slot by 180 degrees, and is led back to the control body on the inner circumferential side of the tube element. Particularly cost-effective anchoring of the traction cable to the distal side of the angled section may be achieved in this way.

An endoscope according to the invention has an insertion tube, the insertion tube having a proximal passive flexible section and a distal angled section. The entire insertion tube, including the passive flexible section and the angled section, is formed from a single tube element.

The distal angled section may have inwardly bent guide protrusions on which a traction cable is supported.

At the transition from the proximal passive flexible section and the distal angled section, the insertion tube may have an inwardly bent bracket on which a guide spring is supported.

Multiple articulated joints may be formed in the circumferential wall of the distal angled section.

The particular articulated joint may have a coupling section that is coupled to an adjacent articulated joint in such a way that an axial movement, but not a radial movement, of the articulated joints relative to one another is blocked, and a guide section that engages with an adjacent articulated joint in such a way that an axial movement of the articulated joints relative to one another is made possible.

The tube element may be made of stainless steel or plastic.

From a control body situated proximally from the proximal passive flexible section, a traction cable may be situated on the inner circumferential side of the tube element, wherein at an articulated joint of the distal angled section situated farthest distally, the traction cable is led through a first slot in a wall of the tube element to the outer circumference of the tube element, around the outer circumference of the tube element, to a second slot in the wall of the tube element to the inner circumference of the tube element, wherein the second slot is opposite the first slot by 180 degrees, and is led back to the control body on the inner circumferential side of the tube element.

The aspects of the present invention described above may be appropriately combined.

BRIEF DESCRIPTION OF DRAWINGS

FIG. 8 shows a cut-away schematic view of a portion of the angled section of the insertion tube according to the invention, a cable guide being shown.

FIG. 9 shows a cut-away perspective view of the cable guide from FIG. 7.

The present invention is described in greater detail below based on exemplary embodiments, with reference to the drawings.

First Exemplary Embodiment

A first exemplary embodiment of the present invention is described below with reference to FIGS. 1 through 16.

Figure 1:
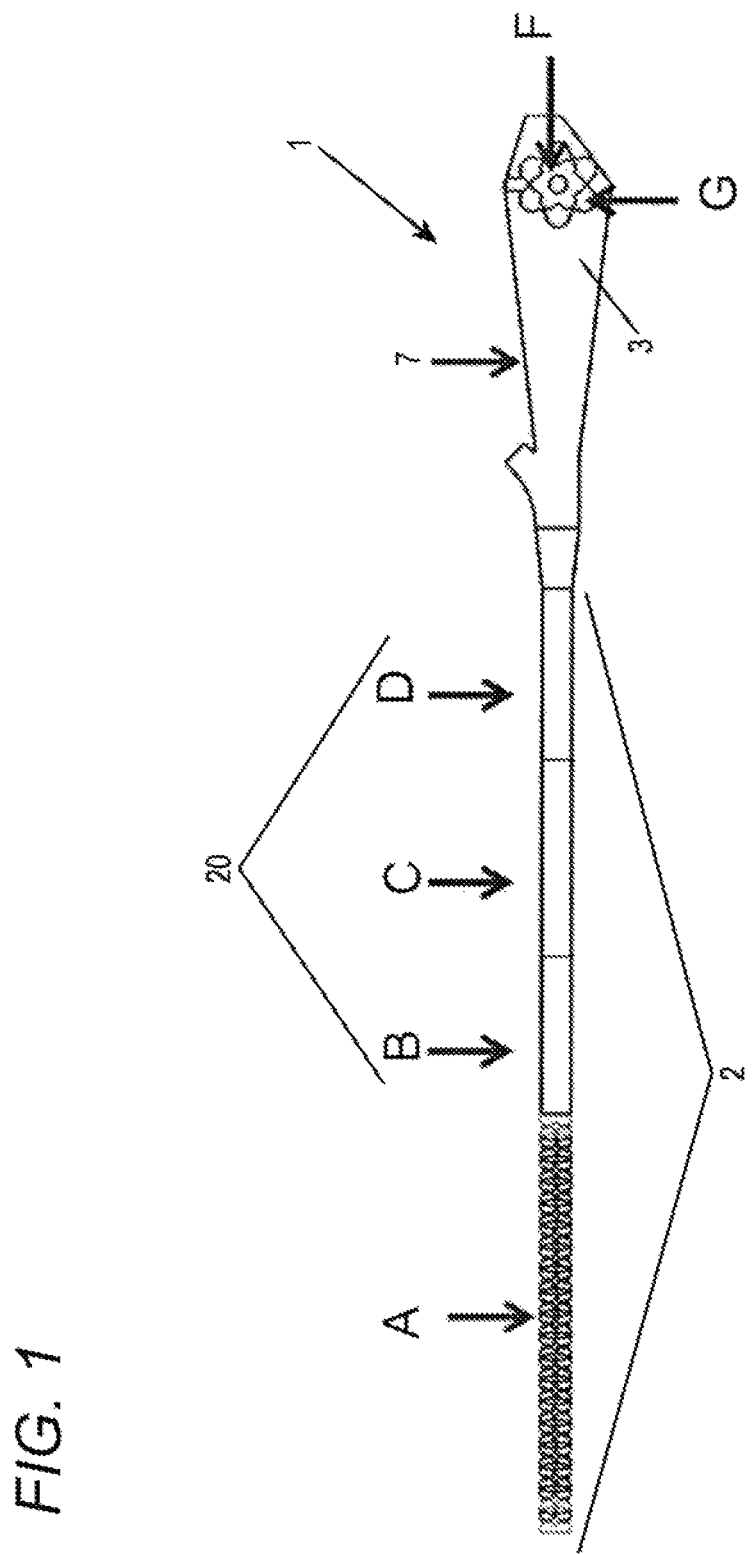
FIG. 1 shows a schematic side view of an endoscope for which the invention may be applied.

Firstly, FIG. 1 shows a schematic side view of an endoscope 1 for which the invention may be applied. It is apparent from FIG. 1 that such an endoscope 1 has an insertion tube 2 situated on the distal side of a control body 3. The control body 3 is used as a control unit for the endoscope 1.

The insertion tube 2 is a cylindrical tube- or hose-like structure.

The insertion tube 2 is described in greater detail below with reference to the direction in which it is inserted into a patient. The insertion tube 2 is inserted with the distal end leading.

The insertion tube 2 has a distal angled section A on the distal side. The angled section A may be laterally bent relative to the proximal portion of the insertion tube 2 by means of one or more control wires (cable pulls). The control wire or cable pull (referred to below only as "control wire") is supported in a guided manner inside the insertion tube 2 on an inner circumferential surface of the insertion tube 2 in the direction of extension of the insertion tube 2.

The distal end of the control wire is anchored on the distal side of the angled section A. The proximal end of the control wire is connected to a control element situated in the control body 3. This control element tensions the control wires in order to achieve desired bending of the angled section A.

Proximal from the angled section A, the insertion tube 2 is designed as a flexible tube element that forms a proximal passive flexible section 20. When the insertion tube 2 is inserted, the flexible section 20 follows the angled section A.

It is shown in FIG. 1 that the flexible section 20 along its longitudinal direction is formed in zones having different degrees of flexibility. For example, the flexible section 20 has a first zone B, a second zone C, and a third zone D, viewed in the proximal direction. The first zone B forms a distal area, the second zone C forms a middle area, and the third zone D forms a proximal area.

Figure 2:
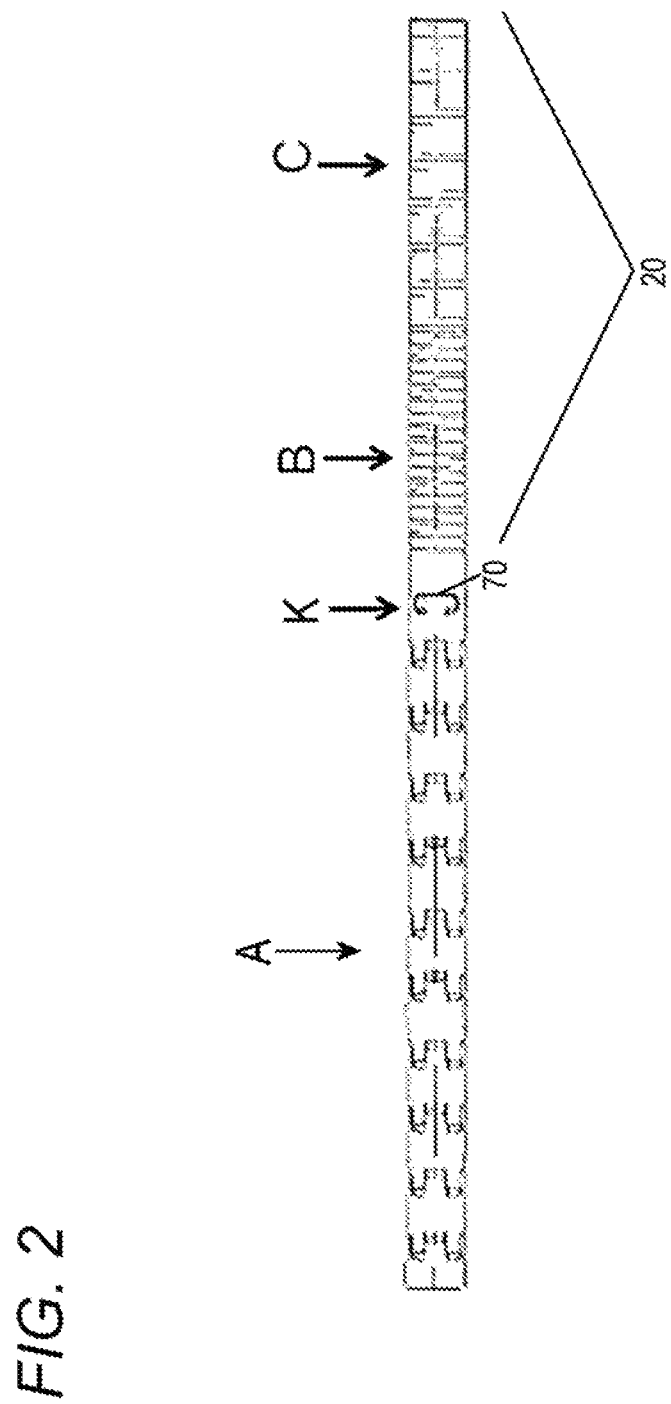
FIG. 2 shows a cut-away schematic view of an insertion tube according to the invention.

The third zone D is not shown in the cut-away illustration in FIG. 2.

To avoid buckling between the angled section A and the first zone B, the first zone B is preferably provided with the highest flexibility of the zones in the flexible section 20. Since the first zone B is provided with very high flexibility, there is no abrupt transition of the flexibility between the angled section A and the first zone B.

The second zone C has less flexibility than the first zone B. The third zone D in turn has less flexibility than the second zone C.

The insertion tube 2 according to the invention is formed from a single piece. That is, two elements are not joined together at the transition from the angled section A to the flexible section 20. Thus, the distal angled section A and the proximal passive flexible section 20 are formed from a single tube or hose having the three zones A, B, and C.

On the proximal side, the insertion tube 2 is fixed to the distal end of the control body 3. The insertion tube 2 may be fixed to the control body 3, for example by means of a locking ring or a sealing ring, or directly. The insertion tube 2 may be adhesively bonded or screwed, for example, to the control body 3. The control body 3 has a first control wheel F, as a first control element, for controlling a control wire or cable pull, and a second control wheel G, as a second control element, for controlling a control wire or cable pull. The first control wheel F may bend the angled section A in a first plane (for example, toward and away from the observer in FIG. 1) by pulling a control wire or cable pull. The second control wheel G may bend the angled section A in a second plane that is perpendicular to the first plane (for example, up and down in FIG. 1) by pulling a control wire or cable pull.

The angled section A may be bent by 200-270 degrees, for example. This is sufficient for most applications. In one special form, the angled section A may even be bent by 300 degrees.

The insertion tube 2 according to the invention and its manufacture are described in greater detail below.

The overall insertion tube 2 is formed from a single tube element or hose element (referred to below simply as "tube element"). The tube element is a tube made of a preferably relatively hard material, particularly preferably stainless steel. However, a tube made of hard plastic may also be used. In principle, however, any material that is usable for medical purposes may be employed.

Cuts are provided in the tube element by a laser cutting machine, as explained in greater detail below. After the cuts are provided, certain subsections of the tube element are bent, as explained in greater detail below. In the manufacture of the base body of the overall insertion tube 2, no further method steps are necessary besides providing cuts and bending. The base body of the insertion tube 2 may be subsequently provided with a control wire and encased with a sheath element.

The individual sections of the insertion tube 2 are described in greater detail below.

Flexible Section 20

The flexible section 20 forms the proximal portion of the insertion tube 2 according to the invention. The flexible section 20 has the three zones B, C, and D, each having different degrees of flexibility.

Figure 3:
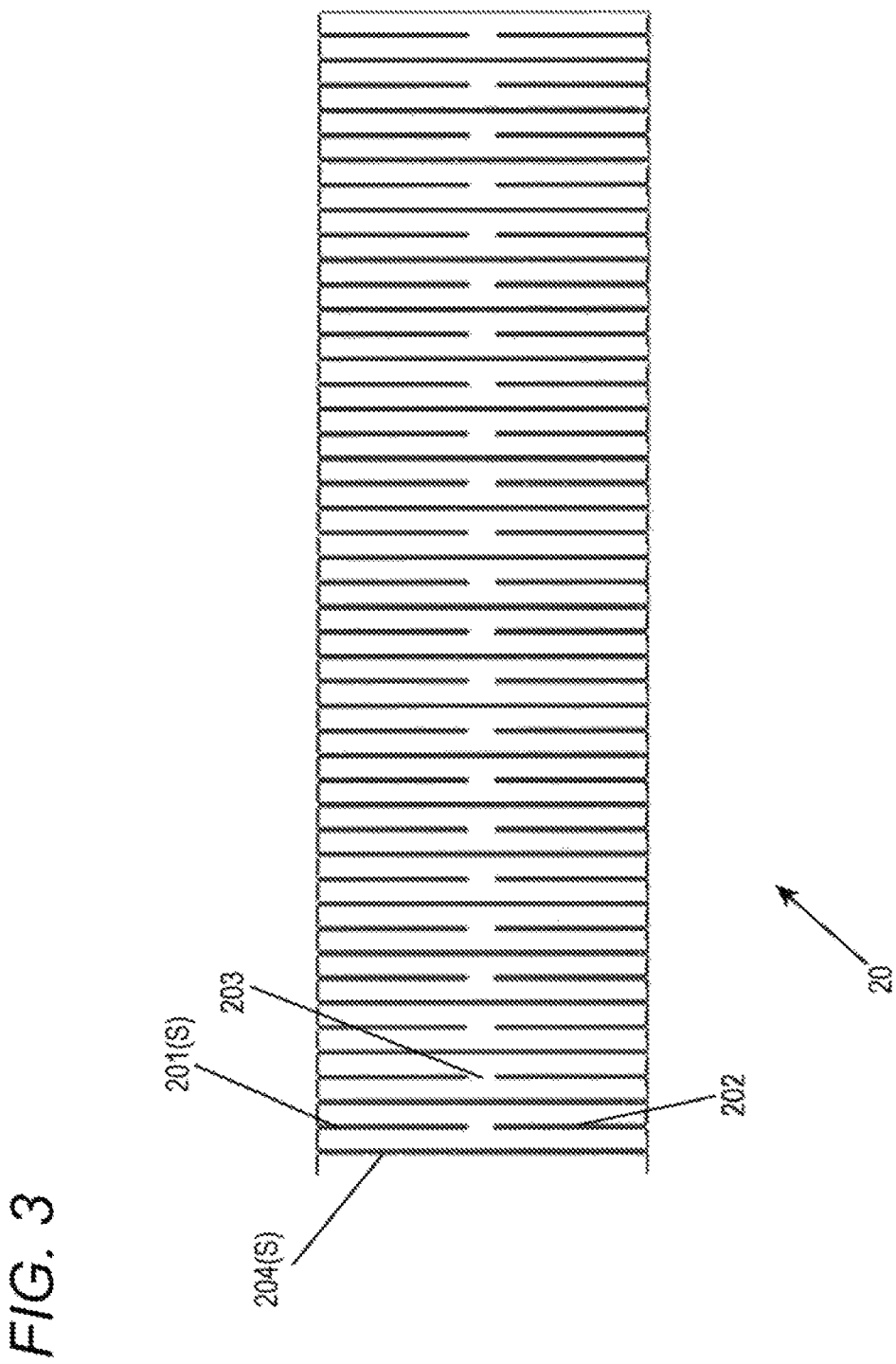
FIG. 3 shows a cut-away schematic view of a portion of a proximal passive flexible section of the insertion tube according to the invention.
Figure 5:
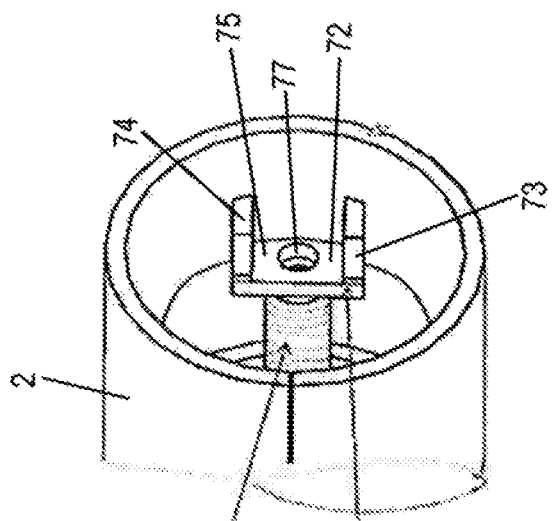
FIG. 5 shows a cut-away perspective view of the guide spring fixing section from FIG. 4, from another side.

FIG. 3 shows one option for forming one of the three zones B, C, and D of the flexible section 20, in a side view.

The flexible section 20 is provided with a plurality of cuts S oriented perpendicularly with respect to the axis of the flexible section 20. More precisely, the cuts S are configured in such a way that a cut 201 is made from above, through the tube element perpendicular to the axis of the tube element, to a depth that ends prior to the center axis area. In addition, a cut 202 is made from below, through the tube element perpendicular to the axis of the tube element, to a depth that likewise ends prior to the center axis area. The cuts 201 and 202 are situated on a plane, and their ends are situated opposite from one another with a space 203 left in between. The space 203 is an uncut space in the center axis area of the tube element.

In addition, similarly as for the cuts 201 and 202, a cut 204 is made from one (for example, left) side (the cut 204 shows a cut from the side of the observer), through the tube element perpendicular to the axis of the tube element, to a depth that ends prior to the center axis area. Furthermore, a cut is made from the opposite (for example, right) side (this cut is not shown in FIG. 3, since it is situated on the other side of the plane of the drawing), through the tube element perpendicular to the axis of the tube element, to a depth that likewise ends prior to the center axis area. These cuts are also situated on a plane, and their ends are situated opposite from one another, likewise with a space left in between. This space is likewise an uncut space in the center axis area of the tube element.

The space 203 between the cuts 201 and 202 and the space between the cut 204 and its associated cut on the opposite side are offset by 90 degrees along the circumferential direction of the tube element.

The cuts 201 and 202 and the cut 204 and its associated cut on the opposite side are adjacently situated, and alternate with one another in the flexible section 20 over the length of the particular zone (see FIG. 3).

The flexible section 20 is thus laterally bendable, with respect to its longitudinal axis, about the spaces.

The individual zones B, C, and D differ in that the spacings between the cuts S in the longitudinal direction, and thus the densities of the cuts S, are different.

The spacing between the cuts S is smallest in zone B. Thus, the density of the cuts S is highest in zone B.

In zone C the spacing between the cuts S is greater than in zone B. In zone D, the spacing between the cuts S is greater than in zone C.

Thus, the flexibility and bendability in zone B are greater than in zone C. In addition, the flexibility and bendability in zone C are greater than in zone D. In other words, the flexibility and the bendability of the respective zones on the flexible section 20 decrease in the proximal direction.

On the proximal side, zone D is provided with an area in which no cuts are made. This area forms a transition to the control body J.

Transition from the angled section A to the flexible section 20

The transition area from the angled section A to the flexible section 20 is denoted as area K in FIG. 2. The angled section A ends in this area K. In other words, the first member of the angled section A, i.e., the member proximally farthest, is distal from the area K.

As shown in FIG. 2, in this area K the wall surface of the tube element is incised by a cut 70 in the shape of a backward letter C. In other words, the cut 70 is made in the tube element in the shape of an incomplete circle. The circle of the cut 70 does not go all the way through on the distal side. The distal side of the cut 70, which does not go all the way through, forms a hinge 71 for a bracket 72. The bracket 72 has a lower lug 73, an upper lug 74, and a bracket middle piece 75. The lower lug 73 adjoins on an upper side of the bracket middle piece 75. The upper lug 74 adjoins on a lower side of the bracket middle piece 75.

The bracket 72 is produced as follows. The location of the cut 70 is specified. A hole 77 is cut in the center of the cut 70. The cut 70 is formed by laser as shown in FIG. 2. The bracket middle piece 75 is supported from the rear side, i.e., by the inner side of the tube element, by a punch. The lower lug 73 is bent inwardly by 90 degrees relative to the bracket middle piece 75. The bend line of the lug 73 relative to the bracket middle piece 75 extends in parallel to the axis of the tube element (in FIGS. 2 and 4, in the directions pointing to the left and to the right). The upper lug 74 is likewise bent inwardly by 90 degrees relative to the bracket middle piece 75. The bend line of the lug 74 relative to the bracket middle piece 75 likewise extends in parallel to the axis of the tube element. The bracket middle piece 75 is subsequently bent inwardly by 90 degrees. The bend line of the bracket middle piece 75 relative to the tube element extends in the plane of the cut perpendicular to the axis of the tube element (in FIGS. 2 and 4, in the directions pointing up and down). In other words, the bracket middle piece 75 is bent inwardly by 90 degrees at the hinge 71. The bracket middle piece 75 is in particular bent inwardly until a distal side edge of the lower lug 73 and a distal side edge of the upper lug 74 rest against the inner circumference of the tube element (see FIG. 5).

The bracket 72 is used to support a guide spring 8. In particular, the proximal face of the bracket middle piece 75 forms a stop surface for the distal end of the guide spring 8. The two lugs 73, 74 support the bracket middle piece 75, and absorb acting pressure forces from the guide spring 8 and further conduct them to the inner circumferential surface of the tube element.

The bracket middle piece 75 has the central hole 77. The hole 77 has a larger diameter than a control wire, and a smaller diameter than the guide spring 8. The control wire is guided in the guide spring 8 in the flexible section 20, passes through the hole 70, and extends further into the angled section A.

In area K, brackets 72 are provided in the numerous (in the present exemplary embodiment, four) control wires used. The brackets 72 are uniformly distributed in the circumferential direction of the tube element.

Angled Section A

A more detailed design of the angled section A is shown in FIGS. 6 through 11.

Figure 7:
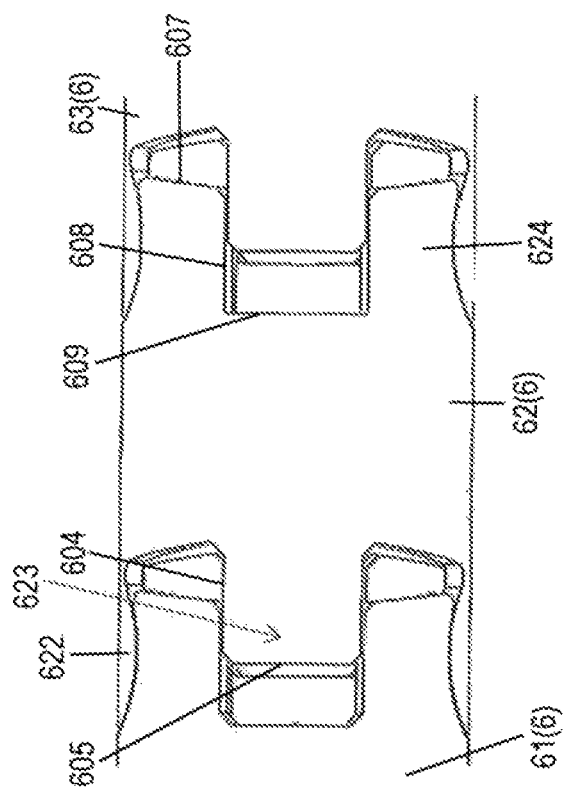
FIG. 7 shows a cut-away schematic view of the portion of the angled section of the insertion tube according to the invention, a view from the direction of an arrow I from FIG. 6 being shown.
Figure 6:
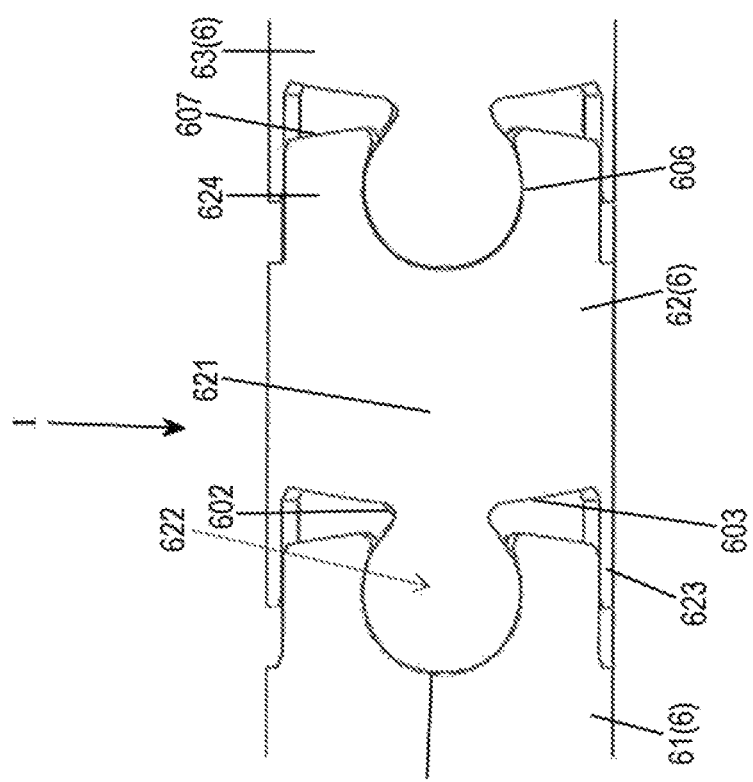
FIG. 6 shows a cut-away schematic view of a portion of the angled section of the insertion tube according to the invention.

The angled section A has individual articulating members 6 situated in the longitudinal direction of the angled section A. The individual articulating members 6 are pivotable relative to one another. FIGS. 6 and 7 show three articulating members 6 situated in succession: an articulated joint 61, an articulated joint 62 proximal from the articulated joint 61, and an articulated joint 63 proximal from the articulated joint 62.

The articulating members 6 have an identical design, except for the articulating member 6 situated distally farthest and the articulating member 6 situated proximally farthest.

The design of the particular articulating member 6 is explained below with reference to the articulating member 62.

The articulating member 62 is formed as a tube section of the stated tube element by laser cutting. The articulating member 62 has distal boundary lines 601, 602, 603, 604, and 605 and proximal boundary lines 606, 607, 608, and 609 on the circumference of the tube element.

The individual distal boundary lines are made up of a circularly shaped head line 601, two neck lines 602, two shoulder lines 603, two arm lines 604, and an arm end line 605. More precisely, the distal side of the articulating member 62 is formed as follows. The circularly shaped head line 601 forms an incomplete circle which at each side merges into a neck line 602 on the proximal side. Each of the two neck lines 602 is adjoined by a shoulder line 603 that extends approximately perpendicularly with respect to the axis of the tube element. Each of the two shoulder lines 603 is adjoined by an arm line 604 that extends in the distal direction, approximately parallel to the axis of the tube element. The two distal ends of the arm lines 604 are connected by an arm end line 605, which similarly extends perpendicularly with respect to the axis of the tube element.

The articulating member 62 thus has a main body 621, from which a first head 622, a first arm 623, a second head 622, and a second arm 623 in each case protrude by 90 degrees toward the distal side along an imaginary circumferential line that extends perpendicularly with respect to the axis of the articulating member 62. The heads 622, 622 thus extend in a first imaginary plane. The arms 623, 623 extend in a second imaginary plane that is offset by 90 degrees with respect to the first imaginary plane. The two heads 622, 622 of the articulating member 62 form a swivel axis for the distally situated articulating member 61.

Each head 622 is formed by a head line 601 on the distal side. A constriction is formed by the neck lines 602, between the head 622 and the main body 621. Each head 622 protrudes farther in the distal direction than does the respective arm 623.

The individual proximal boundary lines are made up of a bent foot line 606, two base lines 607, two straight foot lines 608, and a stomach line 609. More precisely, the proximal side of the articulating member 62 is formed as follows. The bent foot line 606 forms an incomplete circle that is open on the proximal side. At the open ends of the incomplete circle, the bent foot line 606 in each case merges into the base line 607, which in each case extends approximately perpendicularly with respect to the axis of the tube element.

Each of the two base lines 607 is adjoined by a straight foot line 608 that extends approximately parallel to the axis of the tube element in the distal direction. The two distal ends of the straight foot lines 608 are connected by a stomach line 609 which similarly extends perpendicularly with respect to the axis of the tube element.

On the proximal side of the main body 621, the articulating member 62 thus has two feet 624 that extend in the proximal direction. In the direction of extension, each foot 624 has a straight side on the straight foot line 608 and a curved side on the bent foot line 606.

An arm of the proximally situated articulating member 63 is situated so as to be displaceable in the longitudinal direction, in the area between the two straight foot lines 608. A head of the proximally situated articulating member 63 is held so as to be immovable in the longitudinal direction in the area between the two bent foot lines 606. In any event, a slight movement due to play between the inner circumference of the bent foot line and the outer circumference of the circularly shaped head line is possible.

In the unbent state of the angled section A, the stomach line 609 is spaced apart from the arm end line 605 of the proximally situated articulating member 63, as shown in FIG. 7. The arm end line 605 and the stomach line 609 of the proximally situated articulating member 63 are parallel to one another.

In the unbent state of the angled section A, the base line 607 is spaced apart from the shoulder line 603 of the proximally situated articulating member 63, as shown in FIG. 7. The base line 607 and the shoulder line 603 of the proximally situated articulating member 63 may be parallel to one another or approximately parallel to one another or slightly angled with respect to one another, as shown in FIG. 7. Between the base line 607 and the shoulder line 603 of the proximally situated articulating member 63, not only has a single section line been created, but also the material of the tube element has been cut out as a quadrangular piece.

Each head 622 forms a coupling section that is coupled to an adjacent articulating member 6. The feet 624 form a guide section that engages with an adjacent articulating member 6 in such a way that an axial movement of the articulating members 6 relative to one another is made possible.

Figure 10:
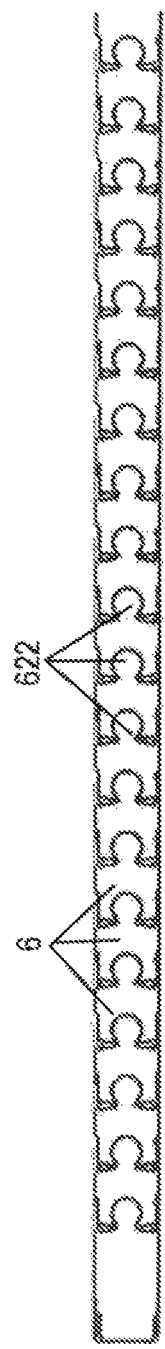
FIG. 10 shows a cut-away schematic side view of the angled section of the insertion tube according to the invention.

FIG. 10 shows a top view of the angled section A with the respective articulating members 6. The heads 622 of the articulating members 6 are visible in the top view.

Figure 11:
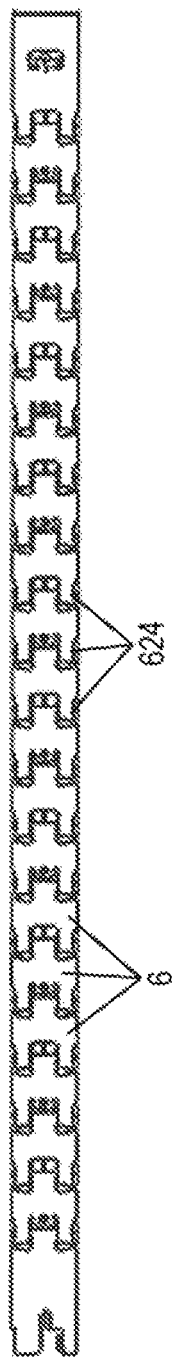
FIG. 11 shows a cut-away schematic top view of the angled section from FIG. 10.

FIG. 11 shows a side view of the angled section A with the respective articulating members 6. The feet 624 of the articulating members 6 are visible in the side view.

The articulating member 6 situated distally farthest has no head, and is shown in FIGS. 2 and 10 through 14.

Figure 4:
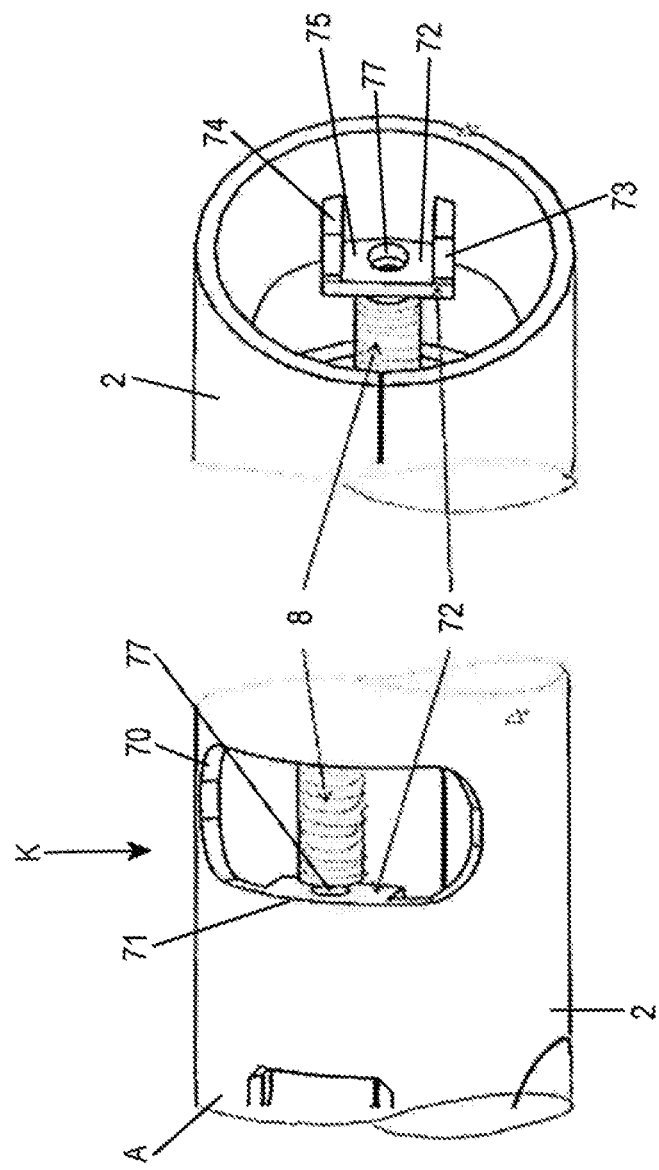
FIG. 4 shows a cut-away schematic view of a transition area between the distal angled section and the proximal passive flexible section of the insertion tube according to the invention, a guide spring fixing section being shown.

The articulating member 6 situated proximally farthest has no foot, and is shown in FIGS. 2, 4, and 11.

In the exemplary embodiment, the angled section A may be bent in two angular directions, namely, upwardly and downwardly in FIGS. 6 and 7 (and FIG. 10), wherein the respective heads 622 of the articulating members 6 form bending axes of the articulating members 6. In other words, the angled section A in FIG. 10 is pivotable upwardly and downwardly. In the illustration in FIG. 11, the angled section A is pivotable toward and away from the observer.

As shown in FIGS. 8 and 9, the stomach line 609 forms a hinge section for a cable guide lug 630. The cable guide lug 630 extends from the stomach line 609. A material section that extends along the straight foot line 608 to the arm end line 605 of the proximally situated articulating member 63 is taken for the cable guide lug 630. The cable guide lug 630 is hinged and bent inwardly by 90 degrees at the stomach line 609. The cable guide lug 630 has a central hole 631. The diameter of the hole 631 is larger than that of the control wire.

Each of the articulating members 6 includes the cable guide lugs 630 with the hole 631, so that for a specific control wire, the cable guide lugs 630 are situated in succession in the longitudinal direction of the angled section A. The cable guide lugs 630 are used as guide protrusions on which a control wire is supported. The cable guide lugs 630 thus guide their assigned control wire through the angled section A.

The articulating members 6 may be situated on the angled section A in such a way that their heads point in the proximal direction, as shown in FIG. 10. Alternatively, the articulating members 6 may be situated on the angled section A in such a way that their heads point in the distal direction, as indicated in FIG. 6.

Figure 12:
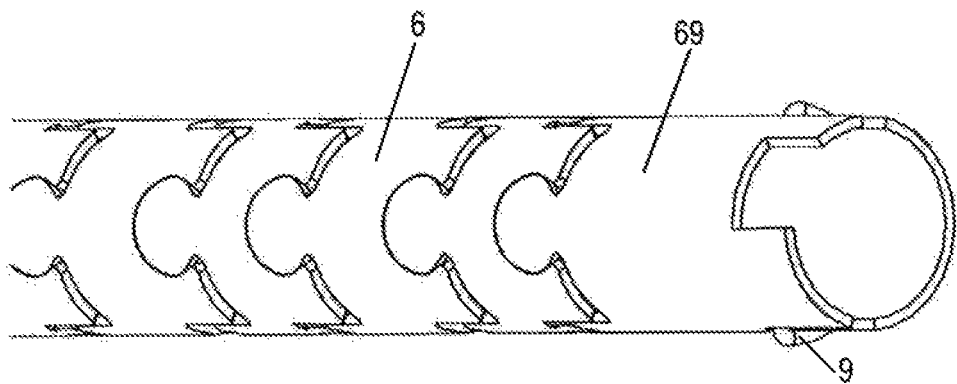
FIGS. 12 through 14 each show a cut-away perspective view of the distal end of the angled section.
Figure 13:
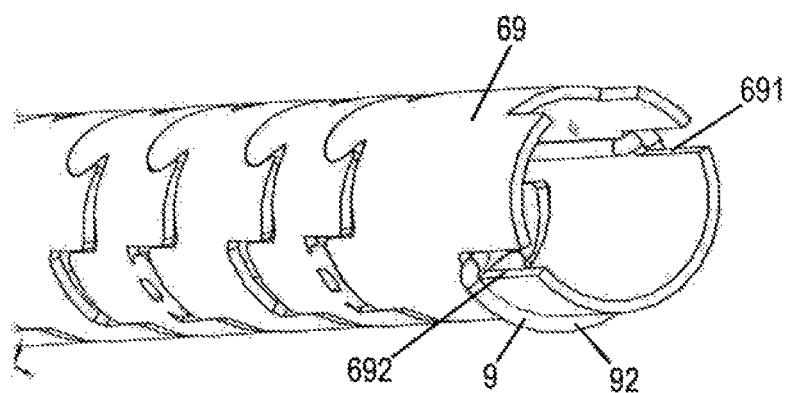
Figure 14:
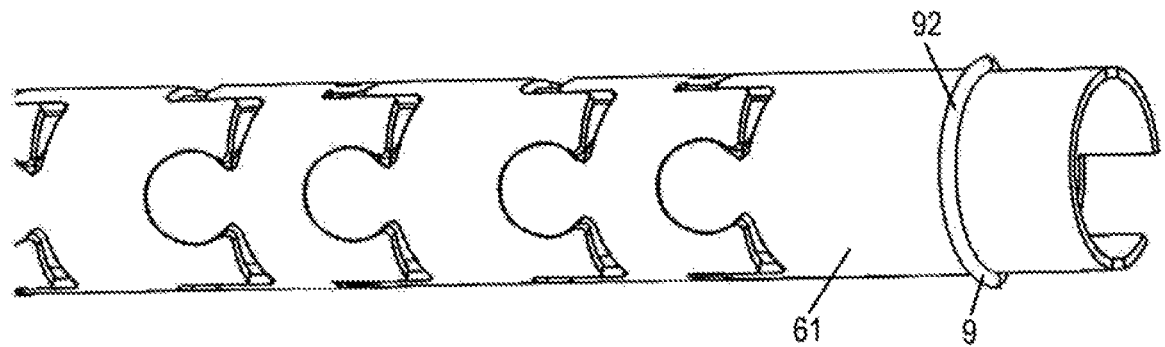

The distal end of the angled section A is shown in FIGS. 12 through 14. The articulating member 69 of the angled section A situated farthest on the distal side is apparent in FIGS. 12 through 14. The distal side of the control wire 9 is anchored in this articulating member 69 situated farthest on the distal side. The control wire 9 extends from the control body 3 to the articulating member 69 of the angled section A situated farthest on the distal side.

Fastening of the Control Wire

Figure 16:
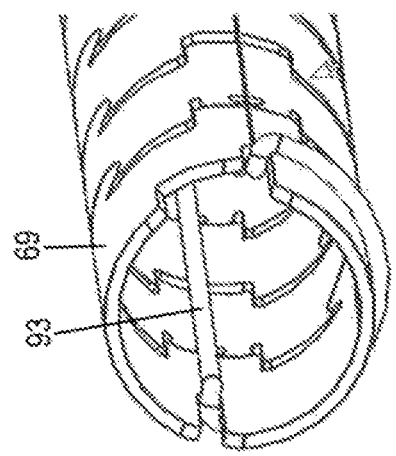
FIG. 16 shows a view, corresponding to FIG. 15, from another side.
Figure 15:
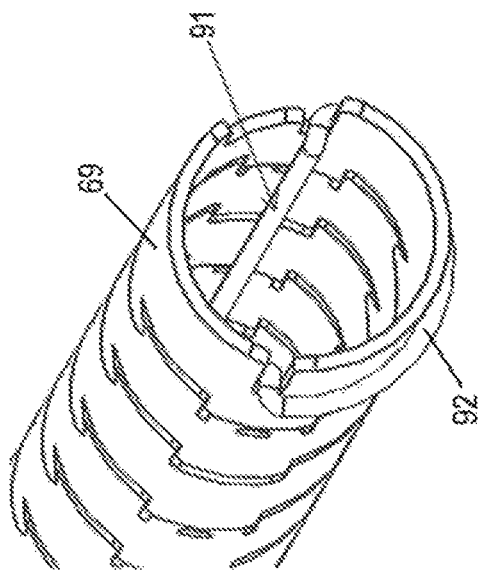
FIG. 15 shows a cut-away perspective view of the traction cable anchor on the distal end of the angled section.

The fastening of the control wire 9 is shown in detail in FIGS. 15 and 16.

The control wire 9 is fastened to the control wheel G in the control body 3. When the control wheel G is rotated in a tensioning direction, the control wire 9 is tensioned. When the control wheel G is rotated in the tensioning relief direction opposite from the tensioning direction, the control wire 9 is relieved of tension.

The control wire 9 runs from the control body 3, extending in the insertion tube 2, to the articulating member 69, forming a first section 91. This first section 91 of the control wire 9 extends along the inner circumference of the insertion tube 2. This first section 91 of the control wire 9 is denoted by reference numeral 91 in FIG. 15. A slot 691 that passes through the circumferential wall of the articulating member 69 and extends in the longitudinal direction of the articulating member 69 is formed on the distal side of the articulating member 69 (see FIG. 13). Another similar slot 692 is provided on the distal side of the articulating member 69, diametrically opposite from the slot 691.

The control wire 9 extends on the inner circumference of the articulating member 69 in the distal direction, and passes outwardly through the slot 691, is wound on the outer circumference of the articulating member 69 in the circumferential direction of the articulating member 69 until reaching the slot 692, passes inwardly through the slot 692, and extends on the inner circumference of the articulating member 69 in the proximal direction to the control wheel G in the control body 3.

The control wire 9 is thus divided into a first section 91 that extends from the control wheel G in the control body 3 to the slot 691, a second section 92 that extends from the slot 691 on the outer circumference of the articulating member 69 in the circumferential direction of the articulating member 69 to the slot 692, and a third section 93 that extends from the slot 692 to the control wheel G in the control body 3.

The control wire 9 is tensioned, and the angled section A is thus bent, by rotating the control wheel G in the tensioning direction, due to the fact that the third section 93 that is anchored on the articulating member 69 is pushed in the proximal direction. The third section 93 of the control wire 9 thus forms a distal anchoring section of the control wire 9.

Manufacturing Method

The insertion tube 2 according to the invention is manufactured from a single tube element that is cut by laser. The tube element is made of a relatively hard material such as stainless steel, or also a suitable hard plastic. Due to the cuts, the initially hard tube element becomes flexible, but maintains its rigidity.

The cuts create the respective lateral indentations S in the proximal passive flexible section 20, the hole 77, the cut 70 in the transition area K, the hole 631, the respective articulating members 6 in the distal angled section A, and the slots 691, 692. This sequence is not to be construed as limiting. For example, the slots 691, 692 may be cut before the articulating members 6. In addition, the order of the cuts may also be reversed.

The flexibility and also the rigidity of the tube element may be controlled based on the shape, arrangement, and size of the cuts.

The location of the particular cuts may be calculated in advance and predetermined. The predefined data for the particular cuts may be input into a programmable laser cutting machine in order to automatically produce the insertion tube 2.

The individual articulating members 6 are completely cut out, and form separate bodies that are connected only in a form-fit manner.

After the laser cutting of the tube element, the brackets 72 and the cable guide lugs 630 are bent inwardly. The blank for the insertion tube 2 is finished in this way.

The control wire 9 may now be inserted and fastened in this blank for the insertion tube 2. The blank for the insertion tube 2 may be fastened to the control body 3. In addition, a covering, preferably made of metal, that encloses the blank for the insertion tube 2 and shields the electrical control system may be applied to the blank for the insertion tube 2, and an elastic sheath made of plastic or rubber may be fitted on same. The plastic or rubber elastic sheath may be subjected to thermal shrinkage.

Second Exemplary Embodiment

A second exemplary embodiment of the present invention is described below with reference to FIGS. 17 through 19.

In the first exemplary embodiment, the individual articulated joints are formed in the bending section based on cuts in such a way that the cuts have protrusions and depressions in the direction of extension of the endoscope. The protrusions rest in the depressions of the adjacent articulated joint to allow a swivel movement of the articulated joint. In other words, in the first exemplary embodiment the individual articulated joints are connected in a form-fit manner.

Figure 17:
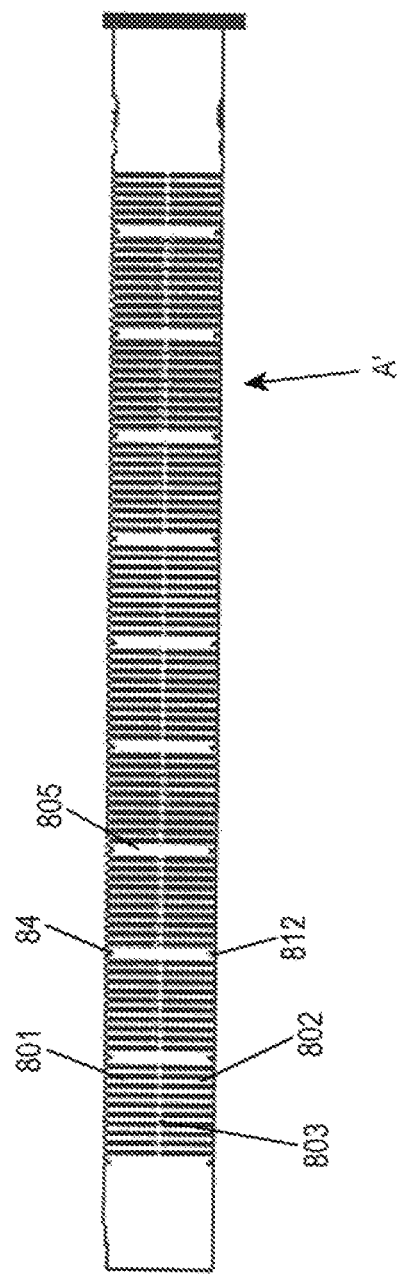
FIG. 17 shows a bending section of a second exemplary embodiment in a side view.
Figure 18:
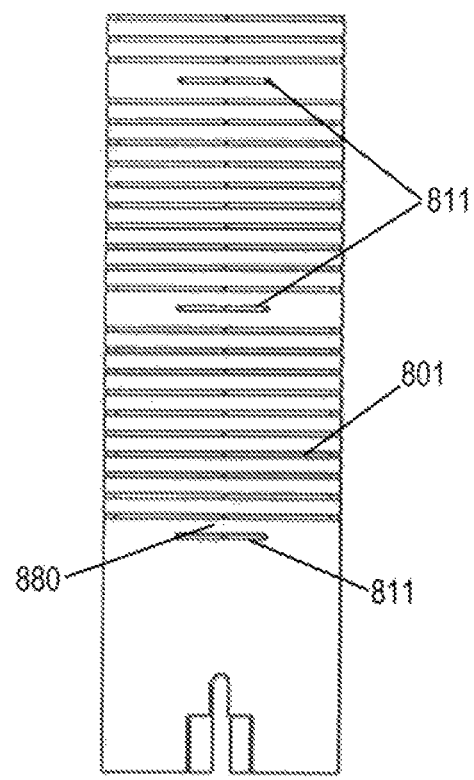
FIG. 18 shows a top view of a distal area of the bending section of the second exemplary embodiment.
Figure 19:
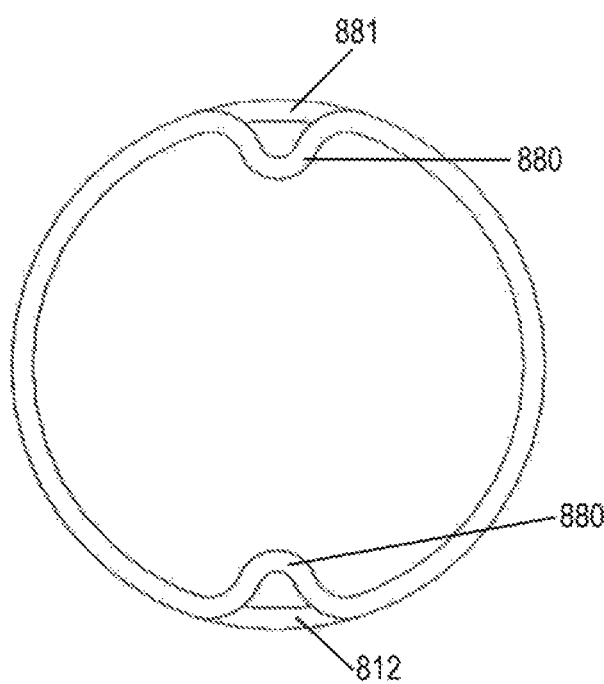
FIG. 19 shows a cross-sectional view of the bending section of the second exemplary embodiment.

FIGS. 17 through 19 show the angled section A' as a bending section of the second exemplary embodiment. In the second exemplary embodiment, only straight cuts 801, 802, 811, 812 are provided in the bending section A'.

The bending section A' is provided with a plurality of cuts 801, 802 oriented perpendicularly with respect to the axis of the bending section A'. More precisely, the cuts 801, 802 are designed in such a way that a cut 801 is made from above, through the tube element perpendicular to the axis of the tube element, to a depth that ends prior to the center axis area. In addition, a cut 802 is made from below, through the tube element perpendicular to the axis of the tube element, to a depth that likewise ends prior to the center axis area. The cuts 801 and 802 are situated on a plane, and their ends are situated opposite from one another with a space 803 left in between. The space 803 is an uncut space in the center axis area of the tube element. The cuts 801 are parallel to one another. The cuts 802 are analogously likewise parallel to one another.

The straight cuts 801, 802 function as an articulated joint and allow the bending movement of the bending section A'.

A predefined number of successive cuts 801 (and analogously 802, of course) in the longitudinal direction of the bending section A' are combined to form a group. In FIG. 18, every 10 cuts 801 belong to a group, wherein the number of cuts 801, 802 for each group may be appropriately selected as desired. The more cuts 801, 802 a group has, the larger the bending angle in the area of this group.

Each group of cuts 801, 802 is delimited in the longitudinal direction of the bending section A' by an annular section 805 having short cuts 811, 812.

More precisely, the short cuts 811, 812 are designed in such a way that a short cut 811 is made from above, through the tube element perpendicularly in the direction of the axis of the tube element, to a very small depth, as shown in FIG. 17. This small depth may be, for example, one-tenth to one-twentieth the diameter of the tube element. This results in a short length of the particular cut 811, 812, as shown in FIG. 18, in which short cuts 811 are shown from above. The length of the short cuts 811, 812 may be appropriately selected as desired.

In addition, a respective short cut 812 from below is made, similarly as for the short cuts 811 from above. The cuts 811 are parallel to one another. The cuts 812 are analogously likewise parallel to one another.

The short cuts 811 and 812 each form a pair, and in each case are situated on a plane, and their ends are situated opposite from one another with a space left in between which forms the annular section 805. The annular section 805 is a section of the tube elements having only one pair of short cuts 811, 812.

The material of the tube element situated adjacent to the particular short cuts 811, 812 forms a strip section. This strip section forms a cable guide lug 880 when it is bent toward the center of the tube element, as shown in FIG. 19. A traction cable may thus be guided in the space that is formed between the outwardly pointing face of the strip section of the cable guide lug 880 and the inner circumferential surface of the tube element that is adjacent in the longitudinal direction.

The straight cuts 801, 802 may be provided on the bending section A' in such a way that the rigidity is similar to that in the first exemplary embodiment.

The machine run time necessary for manufacturing the articulated joints and cable guide lugs may be reduced significantly by providing the straight cuts 801, 802, 811, 812, thus lowering the production costs.

Further Alternatives

In the exemplary embodiment, viewed in the proximal direction the flexible section 20 has a first zone B, a second zone C, and a third zone D having different degrees of flexibility. The number of zones or areas with different flexibilities is not limited. The flexible section 20 may also have more or fewer zones with different flexibilities. The invention is also applicable to an insertion tube in which the flexible section 20 has a uniform flexibility throughout.

In the exemplary embodiment, the tube element of the insertion tube 2 is made of stainless steel. The invention is not limited thereto. The material of the insertion tube 2 may be any given material having sufficient rigidity, such as a hard plastic. In another alternative, Nitinol (a nickel-titanium alloy) may be used as the tube material. This material has the property, among others, of so-called superelasticity; i.e., it may be elastically deformed over a wide range without being permanently distorted.

In one alternative, cuts are provided in the tube element by a laser cutting machine. These cuts may be provided very precisely. Therefore, manufacture by laser is preferred. In principle, however, it is conceivable to also make these cuts by other manufacturing methods such as sawing, wire sawing, etc.

In the exemplary embodiment, the angled section A may be bent in two angular directions, namely, upwardly and downwardly in FIGS. 6 and 7. In one alternative, the individual articulating members 6 may be designed in such a way that their heads 622, from articulating member 6 to articulating member 6, are rotated with an offset of 90 degrees about the axis of the angled section A (axis of the articulating members 6). In this alternative, the angled section A may be bent in four angular directions, namely, upwardly and downwardly, and toward and away from the observer, in FIGS. 6 and 7, respectively.

In the alternative in which the angled section A may be bent in four angular directions, two control wires 9 may be used that extend in the insertion tube 2 with an offset of 90 degrees relative to one another. The articulating member 92 is then provided with four distal slots, which likewise are offset by 90 degrees relative to one another.

In the exemplary embodiment, a particular articulating member 6 has a design with the described shape. The invention is not limited with regard to the shape of the articulating member 6. It is sufficient for articulating members that are coupled to one another, and that allow a deflection movement of the angled section A, to be cut in the angled section A.

The invention may be advantageously used in a duodenoscope, a gastroscope, a colonoscope, or a similar endoscope. The principle of the invention may also be applied to any other given type of endoscope.

The principle of the invention may also be applied to other medical devices that use an insertion tube.

REFERENCE SIGNS LIST 1 endoscope
2 insertion tube
3 control body
6 articulating member
8 guide spring
9 control wire 20 flexible section
61 articulating member
62 articulating member
63 articulating member
69 articulating member situated farthest on the distal side
70 section
71 hinge
72 bracket
73 lower lug
74 upper lug
75 bracket middle piece
77 hole
91 first section of the control wire
92 second section of the control wire
93 third section of the control wire
201 cut from above
202 cut from below
203 uncut space
204 cut from the side
601 head line
602 neck line
603 shoulder line
604 arm line
605 arm end line
606 bent foot line
607 base line
608 straight foot line
609 stomach line
621 main body
622 head
623 arm
624 foot
630 cable guide lug
631 central hole
691 slot
692 slot
801 cut from above
802 cut from below
803 uncut space
805 annular section with short cuts
811 short cut from above
812 short cut from below
880 cable guide lug
A angled section
A' angled section
B first zone (distal area)
C second zone (middle area)
D third zone (proximal area)
F first control wheel (first control element)
G second control wheel (second control element)
J control body housing
K transition area
S lateral indentation on the flexible section

The invention claimed is:

1. An endoscope comprising:
an insertion tube comprising:
a proximal passive flexible section; and a distal angled section wherein the entire insertion tube is formed from a single tube element, and
an inwardly bent bracket on which a guide spring is supported, the inwardly bent bracket located at a transition from the proximal passive flexible section to the distal angled section.

2. The endoscope according to claim 1, wherein
the distal angled section has inwardly bent guide protrusions on which a traction cable (9) is supported.

3. The endoscope according to claim 1, wherein
multiple articulated joints are formed in the circumferential wall of the distal angled section.

4. The endoscope according to claim 3, wherein
a particular articulated joint has a coupling section that is coupled to an adjacent articulated joint in such a way that an axial movement, but not a radial movement, of the articulated joints relative to one another is blocked, and a guide section that engages with an adjacent articulated joint in such a way that an axial movement of the articulated joints relative to one another is made possible.

5. The endoscope according to claim 1, wherein
the tube element is made of stainless steel.

6. The endoscope according to claim 1, wherein
the tube element is made of plastic.

7. The endoscope according to claim 1, wherein
the tube element is made of a nickel-titanium alloy.

8. The endoscope according to claim 1, wherein
from a control body situated proximally from the proximal passive flexible section, a traction cable is situated on the inner circumferential side of the tube element, and at an articulated joint of the distal angled section situated farthest distally, the traction cable is led through a first slot in a wall of the tube element to the outer circumference of the tube element, around the outer circumference of the tube element, to a second slot in the wall of the tube element to the inner circumference of the tube element, wherein the second slot is opposite the first slot by 180 degrees, and is led back to the control body on the inner circumferential side of the tube element.

* * * * *